United States Patent
Seidel

(10) Patent No.: US 9,012,137 B2
(45) Date of Patent: Apr. 21, 2015

(54) DISINTEGRATION OF CELLULAR COMPONENTS IN WHOLE BLOOD BY FREEZE-THAWING

(75) Inventor: Dietrich Seidel, Feldafing (DE)

(73) Assignee: Thermo Finnigan LLC, San Jose, CA (US)

( * ) Notice: Subject to any disclaimer, the term of this patent is extended or adjusted under 35 U.S.C. 154(b) by 675 days.

(21) Appl. No.: 13/003,859

(22) PCT Filed: Jul. 23, 2009

(86) PCT No.: PCT/EP2009/005388
§ 371 (c)(1),
(2), (4) Date: May 25, 2011

(87) PCT Pub. No.: WO2010/009895
PCT Pub. Date: Jan. 28, 2010

(65) Prior Publication Data
US 2011/0229870 A1    Sep. 22, 2011

Related U.S. Application Data

(60) Provisional application No. 61/083,639, filed on Jul. 25, 2008.

(30) Foreign Application Priority Data

Jul. 25, 2008 (EP) .................................. 08013447

(51) Int. Cl.
*G01N 31/00* (2006.01)
*C12Q 1/00* (2006.01)
*G01N 33/80* (2006.01)

(52) U.S. Cl.
CPC ...................................... *G01N 33/80* (2013.01)

(58) Field of Classification Search
CPC .................................. G01N 1/42; G01N 1/44
See application file for complete search history.

(56) References Cited

U.S. PATENT DOCUMENTS

| | | | |
|---|---|---|---|
| 5,151,348 A | 9/1992 | Lau et al. | |
| 6,403,376 B1 * | 6/2002 | Toner et al. | 435/374 |
| 6,605,454 B2 | 8/2003 | Barenburg et al. | |

FOREIGN PATENT DOCUMENTS

WO    WO 2008/003451 A1    1/2008

OTHER PUBLICATIONS

Luyet et al., "On the Mode of Action of Rapid Cooling in the Preservation of Erythrocytes in Frozen Blood", Biodynamica 9 (178) : 95-124 (1963).*
Meryman, "Cryoprotective agents", Cryobiology 8 (2) : 173-183 (1971), abstract only.*
Teramoto et al., "Supplementary Report on Activity of Aminolevulinic Acid Dehydrase (ALA-D) (Part 1): Determination of ALA-D for the Application to Mass Health Examination", Osaka-shiritsu Daigaku Igaku Zasshi 24 (4-6) : 315-323 (1975).*
Conn et al., "The preservation of blood by rapid freezing for subsequent determination of blood ammonia", J. Lab & Clin Med. 63 (6): 1033-1040 (1964).*
Teramoto et al., J. Osaka City Medical Center 24 (4-6) : 315-323 (1975), English translation pp. 1-17.*
Hayes et al., "Whole Blood Cryopreservation in Epidemiological Studies", Cancer Epidemiol. Biomarkers Prev. 11 : 1496-1498 (2002).*
M. W. Scheiwe, et al.: "An Experimental Study on the Freezing of Red Blood Cells With and Without Hydroxyethyl Starch", Cryobiology, vol. 19, No. 5, 1982, pp. 461-477 (XP002496701).
J. D. Fox, et al.: "Miniaturization of Three Carbohydrate Analyses Using a Microsample Plate Reader" Analytical Biochemistry, Academic Press Inc., New York, vol. 195, No. 1, May 15, 1991, pp. 93-96 (XP024828076).
Q. Chen, et al.: "Quantitative Benedict Test Using Bicinchoninic Acid", Analytical Biochemistry, Academic Press Inc., New York, vol. 182, No. 1, Oct. 1, 1989, pp. 54-57 (XP024821422).
R. E. Brown, et al.: "Protein Measurement Using Bicinchoninic Acid: Elimination of Interfering Substances", Analytical Biochemistry, Academic Press Inc., New York, vol. 180, No. 1, Jul. 1, 1989, pp. 136-139 (XP024821771).
Leibo et al.: "Effects of Freezing on Marrow Stem Cell Suspensions: Interactions of Cooling and Warming Rates in the Presence of PVP, Sucrose or Glycerol", Cryobiology vol. 6, No. 4, 1970, pp. 315-332.
Greg G. Power et al., "A novel method of measuring reduction of nitrite-induced methemoglobin applied to fetal and adult blood of humans and sheep". J. Appl Physiol, vol. 103; pp. 1359-1365, Oct. 2007.

* cited by examiner

*Primary Examiner* — Sandra Saucier
(74) *Attorney, Agent, or Firm* — Arent Fox LLP

(57) ABSTRACT

The present invention refers to a method of processing a biological fluid which comprises cellular components by a freezing/thawing treatment. The method is particularly useful for preparing biological samples for analyte detection.

13 Claims, No Drawings

DISINTEGRATION OF CELLULAR COMPONENTS IN WHOLE BLOOD BY FREEZE-THAWING

CROSS-REFERENCE TO RELATED APPLICATION

This is a National Stage entry of International Application No. PCT/EP2009/005388, filed Jul. 23, 2009, which claims priority of European Application No. 08013447.1, filed Jul. 25, 2008, which is also a Non-Provisional of U.S. Provisional Application No. 61/083,639, filed Jul. 25, 2008. The disclosure of the prior application is hereby incorporated herein in its entirety by reference.

The present invention refers to a method and device for processing a biological fluid which comprises cellular components by a snap freezing/thawing treatment under conditions to provide substantially quantitative disintegration of the cellular components while substantially no sedimentation, precipitation, denaturation, agglutination and gelation of fluid components occurs. The method is particularly useful for preparing biological samples for analyte detection.

The effect of freezing and the hemolysis of blood cells has been studied in a variety of studies. Scheiwe et al. (Cryobiology 19, 1982, p. 461-477) investigated the freezing of a suspension of isolated and concentrated red blood cells in small glass capillaries down to −196° C. at different linear cooling rates with or without the cryoprotectant hydroxyethyl starch (HES). From the U-shaped curves for hemolysis as a function of the cooling rate it follows that for example for a Hematocrit (Hct) of 0.6 and in absence of HES the cell suspension has to be treated with a cooling rate of approximately 100° C./min in order to achieve 100% hemolysis. Suspensions of red blood cells having a lower Hct of 0.4 and 0.2 respectively, yielded 80 to 90% hemolysis under these conditions. In the presence of HES hemolysis rates of 50 to 60% could be achieved. Cooling rates of approximately 5000° C./min revealed approximately 40% hemolysis.

Rapatz and Luyet investigated the effect of freezing temperature, freezing rates or protective agents such as cryoprotectants on whole blood samples in terms of the preservation of human erythrocytes (Cryobiology 4, 1968, pp. 215-222). The respective experiments have been performed in glass capillaries with an outside diameter of 1.5+/−0.5 mm and a wall thickness of 0.3+/−0.5 mm. In a further publication the authors investigated hemolysis in several animal species after rapid freezing of blood (J. Cell. Physiol. 77, 1970, pp. 373-376). Recent results on hemolysis of red blood cells are also summarized in the review "A review on basic researches on the cryopreservation of red blood cells" (Luyet and Rapatz, Cryobiology 6, 1970, pp. 425-482).

However, none of the publications dealing with the freezing of whole blood samples give a hint how to obtain a processed fluid from a biological sample comprising cellular components so that substantially all cellular components contained in the biological sample are quantitatively disintegrated whereas substantially no sedimentation, precipitation, denaturation, agglutination and gelation of fluid components occurs. There is further no direction to use the processed whole blood in analysis.

The determination of analytes in samples from biological fluids often requires complicated and tedious pretreatment procedures in order to remove cellular components from the fluid sample. Otherwise cellular components or sediments would clog sample injection devices, capillaries, separation columns etc. For example, whole blood contains components, namely erythrocytes, leukocytes and thrombocytes. In order to determine analytes in a blood sample, these cellular components often have to be removed by pre-treatment procedures such as centrifugation, filtration or sedimentation.

With regard to erythrocytes which represent the major blood fraction, sample pre-treatment involves hemolysis using (bio)chemical reagents, osmotic shock, i.e. by hypo- or hypertonic solutions, and/or mechanical treatment. Hemolysis, however, yields a lysate which is composed of blood plasma and so-called ghosts originating from erythrocytes. These ghosts are depleted of hemoglobin and still have the size of native erythrocytes. This means that the ghosts also have to be removed by centrifugation, filtration or sedimentation prior to analysis.

These procedures, however, are often difficult to integrate into an automated test format. This holds especially for a situation in which the target analytes are present in the cytosol or membrane of the cellular components, e.g. immunosuppressive drugs in erythrocytes. In this case, the cellular components either are isolated or enriched by centrifugation and/or filtration prior to the addition of a lysis reagent or they are denatured by addition of a denaturing agent to the original sample, for example a mixture of $ZnSO_4$ and acetonitrile followed by centrifugation.

Just recently, a novel method has been proposed for processing a biological fluid for analyte determination. This method is based on a heat treatment and is suitable for an automated procedure (WO 2008/003451). This method, however, is strongly temperature-dependent within a small temperature range and thus needs a sophisticated temperature control. The process is also limited by $t_{max}$, the temperature at which coagulation occurs. Furthermore, the addition of an organic modifier such as methanol effects the heating process and thus the process parameters. Further, not every analyte contained in a biological fluid is stable during the proposed heat treatment. Hence, this method is less preferred if heat labile analytes have to be determined.

Thus, the underlying problem of the present invention is the provision of a novel processing method of a biological fluid which comprises cellular components under conditions, (i) to provide substantially quantitative disintegration of said cellular components, (ii) not to cause substantial sedimentation, precipitation, denaturation, agglutination and gelation of fluid components, (iii) not to be restricted to a small temperature range, and (iv) to allow the addition of further fluids such as methanol etc. without affecting the process.

The solution of the above problem is achieved by providing the embodiments characterized in the claims.

According to a first aspect the present invention provides a method of producing a processed biological fluid under conditions, (i) to provide substantially quantitative disintegration of said cellular components and (ii) not to cause substantial sedimentation, precipitation, denaturation, agglutination and gelation of fluid components.

comprising the steps of a) providing a biological fluid which comprises cellular components, b) freezing said biological fluid, and c) thawing the frozen fluid of step a).

A further aspect of the present invention is a processed biological fluid comprising substantially quantitatively disintegrated cellular components which is substantially free from sedimentation, precipitation, denaturation, agglutination and gelation products. Preferably, the biological fluid is undiluted, i.e. no further fluid is added during or before the processing.

Still a further aspect of the present invention is a method of determining an analyte in a biological fluid sample, wherein the biological fluid is processed as described above and the analyte is determined in the processed biological fluid.

Still a further aspect of the present invention is a device for processing a biological fluid, which comprises cellular components, wherein the device comprises:

(a) a fluid processing unit which is at least partially freezable/heatable, (b) a cooling element for freezing a predetermined part of the fluid processing unit, (c) a heating element for heating a predetermined part of the fluid processing unit, (d) optionally a fluid transportation element, e.g. a pumping element, (e) a control element for controlling the freezing/heating of the fluid under conditions
  (i) to provide substantially quantitative disintegration of said cellular components and
  (ii) not to cause substantial sedimentation, precipitation, denaturation, agglutination and gelation of fluid components, (f) optionally a cleaning element and (g) optionally a sample analyzing element.

Surprisingly, the present inventor has found that a complete disintegration of cellular components, preferably cells or cell clusters from higher organisms, more preferably animal cells such as mammalian cells including human cells, and most preferably blood cells such as erythrocytes, leukocytes and/or thrombocytes in biological samples may be achieved by a freezing/thawing treatment under predetermined conditions of time and temperature. The freezing/thawing treatment according to steps b) and c) of the inventive method may be performed at least once, preferably twice or most preferably three times or even more.

By means of the treatment according to the present invention, the cellular components contained in a biological fluid are substantially quantitatively disintegrated to generate subcellular particles without substantial sedimentation, precipitation, denaturation, agglutination and/or gelation of fluid components. Thus, a processed biological fluid according to the present invention comprises subcellular particles as well as liquid components comprising ions, gases, low molecular substances like sugars, and proteins.

"Biological fluid" by means of the present invention relates to a biological suspension comprising cellular components and liquid components, and which is selected from a body fluid or a cell culture fluid. The cellular components are cells, cell clusters or cell ghosts, the liquid components are plasma, urine, saliva and the like or cell culture media. Particular examples for body fluids are whole blood, urine, cerebrospinal fluid, saliva, lymph fluid, and for cell culture fluids mammalian cell culture fluids.

"Cellular components" as used in the present invention relates to cells, cell clusters or cell ghosts, particularly erythrocyte ghosts.

Within the context of the present invention "subcellular particles" contained in a processed biological fluid relate to cell fragments such as membrane vesicles which are generated by the inventive method and which consists of very small spheres and/or very small particles of resealed membranes, characterized in that they a) do not sediment on standing in a time of at least about 24 hrs, and b) do not sediment after centrifugation for a time of at least 10 min at a g-force of about 3000 unlike erythrocyte-ghosts (size of about 5-8 μm) or intact cells, and c) sediment after centrifugation for at time of at least 20 min at a g-force higher than about 11000.

"Substantially quantitative disintegration of cellular components" contained in a biological sample fluid within the context of the present invention means that about 70%, preferably about 80%, more preferably about 90% and even most preferably about 100% of the cellular components are disintegrated into subcellular particles.

In this context it was found by the present inventor that the desired disintegration of about 100% could be achieved e.g. with native anti-coagulated whole blood by the treatment according to the present invention, wherein this rate of disintegration is independent of the hematocrit which may vary from 0.1 to 0.6.

Processed whole blood or processed hemolytic blood according to the present invention comprises plasma and disintegrated blood cells, i.e. disintegrated erythrocytes, leucocytes and thrombocytes. Plasma within the processed, i.e. cell disintegrated, whole blood comprises ions such as sodium, chloride, potassium, magnesium, phosphate and calcium ions, low molecular substances like monosaccharides, hormones, gases, nutritional substances like lipids or vitamines, metabolic substances such as urea or uric acid, as well as plasma proteins such as albumins and globulins. "Whole blood" according to the present invention relates to blood in which the blood cells are substantially intact, "hemolytic blood" relates to whole blood in which hemolysis has taken place.

It was found that also hemolytic samples, i.e. erythrocyte ghosts, can be substantially disintegrated as indicated above. It was further found that also leukocytes and/or thrombocytes present in whole blood can be substantially quantitatively disintegrated as indicated above.

Hence, these processed biological fluids comprising subcellular particles allow further processing by fluidic separation systems and do not clog these systems.

The obtained biological fluid may be free from added reagents so that it is characterized as being not diluted. Hence, this biological fluid can be further processed in a quantitative manner without an additional dosing.

The processed biological fluid is thus suitable for use in in situ analysis techniques such as solid-phase extraction (SPE), undiluted on line/off line SPE or techniques requiring spotting, sampling or dispensing, e.g. on a microfluidic device.

Freezing within the inventive method may be performed by snap freezing. Snap freezing may be carried out by immersing the sample contained in a sample device by a) immersing said sample device into a cryogenic fluid which is contained in an insulated tank, b) immersing said sample device into the vapour-phase of a cryogenic fluid, or c) inserting said sample device into a sleeve which tightly fits to the sample device and which is immersed into a cryogenic fluid or into the vapour-phase of a cryogenic fluid.

"Cryogenic fluid" as used in the present invention relates to a material that is liquid in the temperature range that is necessary to freeze aqueous solutions, preferably at a temperature below $-90°$ C. The cryogenic fluid can be a cold gas or a cryogenic liquid. Cryogenic liquids are chilled liquids like argon, helium, hydrogen, nitrogen, oxygen, methane, carbon dioxide, nitrous oxide, isopentane, hexane, or ethanol and other fluids like hydrocarbon fluids or mixtures thereof. In a preferred embodiment liquid nitrogen is used.

During freezing the biological fluid is frozen to a temperature of $-20°$ C. to $-196°$ C., preferably of $-120°$ C. to $-190°$ C. of the inventive method. The respective cooling rates range from about $1260°$ C./min to about $12600°$ C., preferably of about 2000° C./min to about 5000° C./min and are most preferred about 2500-3500° C./min, e.g. about 3150° C./min.

Preferably, the frozen fluid is subsequently subjected to a thawing treatment to a temperature of at least room temperature, preferably to at least 40° C., most preferably to at least 50° C. and up to 60° C. or even up to 75° C.

For thawing, the heat treatment may be carried out while the sample device containing the frozen sample is inserted into a sleeve which tightly fits to the sample device and which can be heated. The heating may be carried out by any suitable means and may comprise e.g. conductive heating, inductive heating such as microwave treatment, for example as described in U.S. Pat. No. 6,605,454, convective heating, resistive heating and/or heating by laser excitation.

The respective thawing rates range from about 500° C./min to about 11400° C./min, preferably from about 1000° C./min to about 4000° C./min and are most preferred about 1500-2500° C./min.

The time inbetween freezing and thawing may be kept to a minimum, preferably between 1 and 5 sec. Longer time periods are also acceptable, however.

A suitable sample device according to the present invention may be a volumetric is device of a dosing unit and is made of a thermally conductive or inductive material which tolerates temperatures of up to −200° C. Preferred materials are stainless steel, glass or plastic. Most preferred is stainless steel.

The device of the present invention comprises a fluid processing unit, which is at least partially freezable/heatable. This processing unit may preferably comprise a needle, such as an injection needle, a pipette tip, a capillary such as a glass capillary, a syringe or a conduit. Most preferred is an injection needle or pipette tip of a liquid handling system such as an autosampler for HPLC e.g. PAL-autosampler (LEAP-Technologies) or of a pipetting robot e.g. Evoclean (Tecan).

The fluid processing unit may also comprise material for in situ analysis such as chromatographic adsorbent for solid phase extraction (SPE) such as C-18 modified silica, OasisHLB and the like well known in the art.

The lumen/inner diameter of the fluid processing unit, particularly of a needle, glass-capillary or pipette tip, can vary from 0.01-5 mm, preferably from 0.1-2 mm, even more preferably from 0.5-1 mm. Most preferably the lumen/inner diameter of a pipette tip, a glass-capillary or a needle is about 0.3 to about 0.5 mm. Most preferably the lumen/inner diameter of a needle is about 0.3 mm.

The wall thickness of the fluid processing unit, particularly of a device made of plastic or metal, is preferably in the range of about 0.05-0.5 mm.

The completeness of disintegration may be determined by cell counting, e.g. in a Neubauer counting chamber, by microscopic inspection for particular components and/or by lack of sediment formation after centrifugation. In this context, it should be noted that about 95% of cellular blood components are represented by erythrocytes. Thus, the cell count in a blood sample is preferably determined by counting the erythrocytes.

By means of the present invention the cell count in the sample is preferably reduced to 0.1% or less and more preferably to 0.01% or less of the original value. For example, when subjecting a sample with $5 \times 10^6$ erythrocytes per µl to treatment according to the present invention, the cell count is preferably reduced to $5 \times 10^3$ cells or less per µl, more preferably to 500 cells or less per µl. Most preferably, the sample is free from detectable cells. The absence of particular components such as erythrocyte ghosts may also be determined by light-microscopic observation, e.g. up to 100× magnification, and/or by centrifugation for 10 min at up to 3000 g, preferably at up to 7400 g.

For snap freezing, the capillary conduit (or any other fluid processing unit as described above) first is loaded with the sample. This is preferably achieved by segmenting the sample by defined volumes of gas, e.g. air. For example, a first volume of gas may be aspirated into the fluid processing unit, followed by the sample and followed by a second volume of gas. Subsequently, the sample containing fluid processing unit may be a) immersed in a cryogenic fluid or in the vapour-phase of a cryogenic fluid, b) contacted with a surface which is cooled by a cryogenic fluid or the vapour-phase thereof, or c) inserted into a sleeve which tightly fits to the sample device and which is immersed into a cryogenic fluid or into the vapour-phase of a cryogenic fluid.

For the thawing treatment of the present method, the fluid processing unit containing the frozen sample is heated by any suitable means which may comprise e.g. inductive heating such as microwave treatment, for example as described in U.S. Pat. No. 6,605,454, convective heating, resistive heating and/or heating by laser excitation.

For elution from the fluid processing unit, the processed fluid may be displaced by air and/or a further fluid. If only air is used, no dilution of the processed fluid occurs.

The biological fluid may be a body fluid such as whole blood, urine, cerebrospinal fluid, saliva, lymph fluid etc. or fluid from a cell culture, particularly mammalian cell culture or any other biological fluid comprising cellular components, particularly fluids comprising blood cells. More preferably, the biological fluid is whole blood, such as venous, arterial or capillary blood, particularly anticoagulant-treated whole blood, e.g. EDTA-, citrate-, or heparin-treated whole blood. For example, a sample may be taken with an anticoagulant containing blood withdrawal device and directly subjected to further processing as described below.

The sample volume may be varied broadly, e.g. in the range of 1 nl or more, preferably 10 nl or more and up to 1 ml. Thus, the method is preferably suitable for miniaturized applications, e.g. microfluidic devices on chip format, nano LC-MS, MALDI-MS analysis etc.

The method of the present invention does not require any sedimentation and/or precipitation and/or centrifugation steps and/or the addition of chemical/biochemical reagents. Thus, the treatment is preferably carried out without previous removal and/or lysis of cellular components. The method may be carried out in any suitable device, e.g. a single-use device or a reusable device. Preferably, the method is an automated procedure, which may be carried out in an integrated device, i.e. a device into which the fluid sample is transferred, optionally after mixing, e.g. with a further fluid, without pretreatment, particularly without removal and/or lysis of cellular components. Within the device, the sample is preferably directly subjected to the treatment without prior removal and/or a lysis of cellular components. After treatment, subsequent steps, e.g. an analyte determination may be carried out. Most preferably, the treatment is carried out with a substantially native sample, e.g. a sample comprising substantially intact cellular components such as whole blood.

The method of the present invention may include the addition of further fluid to the biological fluid before and/or after processing. The further fluid may be any fluid which is compatible with a biological fluid so that it does not cause precipitation, agglutination or agglomeration. The further fluid may be an organic solvent, preferably in an amount of up to 20% (vol/vol), more preferably in an amount of up to 10% (vol/vol) based on the volume of the biological fluid. The organic solvent is preferably selected from water-miscible solvents such as methanol, ethanol, acetonitrile, dimethyl sulfoxide (DMSO), dimethyl formamide (DMF) and combinations thereof.

Preferably, the further fluid does not substantially effect the disintegration of cellular components. More preferably, the further fluid is an aqueous fluid, e.g. an aqueous buffer solution or a further biological fluid, preferably having an ionic strength corresponding to 0.5-1.4% NaCl, more preferably 0.7-1.2% NaCl and most preferably about 0.9% NaCl.

The further fluid may be a standardisation and/or calibrator fluid comprising a predetermined amount of at least one standardisation and/calibrator compound. The addition of standardisation and/or calibrator compounds is particularly suitable if the treated biological fluid is further analysed by means of chromatographic, spectrometric and/or spectroscopic methods. The standardisation and/or calibrator compounds may be analyte analogues which contain stable isotopes such as $^2H$ and/or $^{13}C$ and thus may be detected by mass spectrometry. Suitable calibrators may also be selected e.g. from Clin-Cal® Matrix Calibrators.

The method also may include the addition of a marker/staining compound for lipids, proteins, peptides, nucleic acids and carbohydrates to the biological fluid before and/or after processing.

The processed fluid preferably has an ionic strength corresponding to 0.5-1.4% NaCl, more preferably 0.7-1.2% NaCl and most preferably a substantially physiological salt concentration. The processed fluid may be free from added reagents, e.g. disintegration reagents and/or detergents. On the other hand, the processed fluid may also comprise organic solvents and/or added aqueous fluid as described above. Most preferably, the processed fluid is disintegrated whole blood.

The present invention also refers to a method of determining an analyte in a biological fluid sample which has been subjected to a treatment as described above. The analyte may be any analyte which may be detected in biological fluids, e.g. a biological compound such as a nucleic acid, a polypeptide, peptide, lipid, sugar, hormone, metabolite, etc. On the other hand, the analyte may be a non-biological compound, e.g. a pharmaceutical compound. In a preferred embodiment, the analyte is an immunosuppressive drug, such as cyclosporin, rapamycin or tacrolimus or related compounds.

The analyte determination in the processed fluid may be carried out according to any known method. For example, the analyte determination may be carried out according to chemical, biochemical and/or physicochemical methods and may comprise a hybridization reaction, an immunological reaction, an enzymatic reaction, e.g. a nucleic acid amplification, a chromatographic analysis, a spectrometric analysis, such as a mass-spectrometric or a NMR analysis and/or a spectroscopic analysis. In an especially preferred embodiment, the invention refers to a method of determining an immunosuppressive drug in a whole blood sample, wherein the whole blood is processed by a treatment as described above and the immunosuppressive drug is determined in the processed whole blood according to standard methods, e.g. by mass-spectrometric (MS) methods.

The inventive method is particularly suitable for bioanalytical and clinical-chemical analysing procedures such as solid-phase extraction (SPE), liquid-liquid extraction (LLE) and the like. Hence, preferred analysing methods in accordance with the present method are SPE, particularly in-situ SPE of target analytes from whole blood, on-line/off-line/in-line extraction methods of target analytes using undiluted cell disintegrated blood such as SPE with or without coupling to HPLC or MS, spotting of cell disintegrated blood onto plates such as MALDI-plates, arrays, microchips and the like, sampling of undiluted disintegrated blood into appropriate containers such as 96-well plates, Eppendorf vials and the like, derivatization and processing of undiluted cell disintegrated blood for e.g. MALDI-MS, and sampling of undiluted cell disintegrated blood onto microfluidic devices such as on Lab-on-a-chips or Point-of-care testing (POCT).

In a further preferred embodiment, the analyte is a clinical-chemical parameter, e.g. a clinical-chemical parameter associated with an inborn metabolic disorder, e.g. phenylketonuria. In this embodiment, the sample is preferably a capillary blood sample which may be obtained from newborns.

In a still further preferred embodiment, the method is suitable for processing blood samples from non-human animals, preferably mice, guinea pigs and rats. For example, the samples may be taken by automated systems and directly processed as described above. A preferred automated system is the Accu Sampler® from DiLab®.

A device of the present invention may also comprise a fluid introduction port, where a sample of a biological fluid may be injected into a fluid processing unit. The fluid may be transported within the device by a transportation element, e.g. a pumping element. The fluid processing unit is at least partially freezable/heatable. The freezable and/or heatable part of the fluid processing unit may be an integral part of the device or removably attached to the device. The fluid processing unit has preferably an inner diameter of about 0.1-0.8 mm.

Thus, a biological fluid can be processed according to the invention either directly in a removable unit, e.g. in a stainless steel needle, or in an integrated unit in a capillary conduit, e.g. a stainless steel capillary.

The cooling element may be a sleeve which tightly fits to the fluid processing unit and which is immersed into a cryogenic fluid or into the vapour phase of a cryogenic fluid. The heating element may be any suitable heating element, e.g. an element for inductive heating, an element for convective heating, an element for resistive heating and/or an element for heating by laser excitation. For example, the heating element may be a heating coil wrapped around a predetermined part of the fluid processing unit or a microwave emitter. The control element provides control of the sample processing, i.e. cooling and heating of the fluid, e.g. by controlling the cooling/heating intensity and/or time in the freezable/heatable part of the fluid processing unit.

The device may optionally comprise a cleaning element which is suitable for cleaning and/or monitoring the cleaning efficiency of the corresponding fluid processing unit or of at least part thereof.

The cleaning element is adapted for carrying out a cleaning for example of the fluid processing unit or a part thereof after a predetermined number of biological fluid processing cycles. Preferably, the cleaning comprises passing a cleaning fluid through the fluid processing unit or a part thereof. The cleaning fluid is capable of removing biological, e.g. proteinaceous residues in the processing unit. The cleaning may involve aspirating and dispensing or flushing of the fluid dosing unit or a part thereof with the cleaning fluid, wherein the fluid processing unit or part thereof is preferably heated. The cleaning efficacy may be controlled by monitoring the presence of biological materials in the fluid processing unit or a part thereof during a cleaning procedure.

In WO 2008/003451 a suitable cleaning procedure for a fluid processing unit is described which at least involves two steps. First, the fluid processing unit has to be flushed with an alkaline NaOCl solution preferably at a temperature at or above 60° C. Under these conditions, residual biological materials are oxidized. In a second step, the efficiency of this treatment is monitored by using a suitable reagent, e.g. an OPA-reagent in order to generate reaction products which can be detected photometrically at 340 nm.

In a preferred embodiment, the present invention provides an alternative cleaning procedure which a) involves only a single treatment step, b) allows the simultaneous performance and monitoring of the cleaning process, c) does not cause corrosion of materials made of metal, and d) is effective at temperatures below 60° C.

This cleaning procedure may be used in the method and device of the present invention. However, it is also applicable in different methods and devices invoicing the transport of biological samples through metal and/or plastic conduits, particularly through conduits.

Thus, a further subject-matter of the invention is the use of an bicinchoninic acid (BCA) reagent (Stoscheck, Meth. Enzymol. 182 (1990), 50-69), preferably an alkaline bicinchoninic acid (BCA)/tartrate/copper reagent, for the cleaning of devices being in contact with biological samples, e.g. whole blood or plasma samples. The BCA reagent, which is e.g. available from Pierce Chemicals, forms a purple-coloured reaction product with Cu(I)-ions in the presence of proteins. This reaction may be monitored continuously at 562 nm. Surprisingly, the BCA reagent is capable of removing biofilms e.g. adhering to interior metal and/or plastic parts of devices being in contact with biological samples, e.g. sample processing devices. The BCA reagent may be contacted with the parts of the device to be cleaned under suitable conditions, e.g. at a temperature up to 60° C.

Thus, it is another object of the present invention to provide a cleaning reagent comprising BCA. The cleaning reagent according to the present invention preferably comprises BCA, metal ions, e.g. copper ions, particularly copper (I) ions, and an aqueous buffer solution, and has an alkaline pH, e.g. a pH of about 10-12, particularly about pH 11. The aqueous buffer solution may comprise a suitable buffer such as a tartrate, bicarbonate, or carbonate buffer, or a combination of such buffers.

Further, the device optionally comprises a sample analysing element. The sample analysing element may be any element which is suitable for analyte detection in a biological sample. Preferably, the sample analysing element comprises a chromatographic element, e.g. an HPLC element, an extraction element, e.g. a solid-phase extraction (SPE) element, a spectrometric element, e.g. a mass-spectrometric or NMR element, a spectroscopic element, an enzymatic and/or immunoassay element and/or a hybridization assay element.

Finally, the device may comprise a processor unit which may transfer data to and/or receive data from a remote control unit. The data transfer may occur online, e.g. by wireless transfer such as via GSM/GPRS/3G data transfer. The remote control unit may be adapted to authorise fluid processing for a respective device, e.g. after payment for carrying out a predetermined number of fluid processing procedures has been received (i.e. pay-per-process).

It should be noted that all preferred embodiments discussed for one or several aspects of the invention also relate to all other aspects.

Further, the present invention is explained in more detail by the following examples.

EXAMPLES

Example 1

Method for Disintegration of Cellular Components, i.e. Erythrocytes, Leucocytes and Thrombocytes Present in Human Whole Blood In a first step, 20 µl of ambient air are aspirated by a syringe/injection needle (stainless steel, inner diameter 0.3 mm; wall thickness 0.2 mm) followed by 10 µl of an anticoagulated whole blood sample from a volunteer (hematocrit 0.42). Finally, again 20 µl of air are aspirated. Then the syringe/injection needle is immersed into an insulated container filled with liquid nitrogen and positioned in such a way that the whole blood sample is located below the surface of the liquid nitrogen. The snap freezing process takes 5 sec under the described conditions, which corresponds to a cooling rate of about 2700° C./min. Thereafter, the syringe/injection needle which contains the frozen sample is immersed within 2 sec into a water bath adjusted to 50° C. and positioned in such a way that the frozen sample is located below the water surface. The thawing time amounts to 8 sec, which corresponds to a heating rate of about 1900° C./min.

Microscopic inspection and cell counting using a Neubauer counting chamber before and after the snap freezing/thawing process revealed that the cellular blood components present in the treated blood sample (erythrocytes $5.2 \times 10^6/\mu l$; leucocytes $6.5 \times 10^3/\mu l$; thrombocyctes $2.2 \times 10^5/\mu l$) were quantitatively disintegrated.

Example 2

Cleaning of the Fluid Processing Unit and Simultaneous Monitoring of the Cleaning Efficiency A stainless steel capillary conduit (internal diameter 0.5 mm; length 10 cm), which had been used for 50 times for the process of snap freezing and thawing of whole blood samples in analogy of Example 1 was cleaned in the following way. A solution of the so-called BCA reagent (bicinchoninic acid, sodium tartrate, sodium bicarbonate, sodium carbonate, 4% cupric sulfate, in 0.1 N NaOH; Pierce Chemical), which originally is used for the determination of proteins, was pumped through the capillary conduit at a flow rate of 200 µl/min. In addition, the capillary conduit was immersed in a water bath heated to 50° C. The eluting liquid was passed through a USV/UIS detector and the absorption was monitored at 562 nm. Complete cleaning, i.e. removal of residual proteins and the like was achieved after the signal reached again the baseline, in this case after 9 min.

The invention claimed is:

1. A method of producing processed whole blood under conditions,
   (i) to provide substantially quantitative disintegration of said cellular components, and
   (ii) not to cause substantial sedimentation, precipitation, denaturation, agglutination and gelation of fluid components,
   comprising the steps of
   a) providing whole blood which comprises cellular components,
   b) optionally adding a further fluid to the whole blood in an amount of up to 10% (vol/vol), wherein the further fluid is a water-miscible solvent selected from the group consisting of methanol, ethanol, acetonitrile, dimethyl sulfoxide (DMSO), dimethyl formamide (DMF), and combinations thereof, or wherein the further fluid is an aqueous fluid, c) freezing said whole blood, d) thawing the frozen whole blood of step a) at a thawing rate of about 500-2500° C./min, and e) obtaining processed whole blood which comprises substantially quantitatively disintegrated cellular components, wherein the further fluid is added in an amount which does not prevent step e) and does not cause substantial sedimentation, precipitation, denaturation, agglutination and gelation of fluid components.

2. The method of claim 1, wherein the whole blood is frozen to a temperature of −20° C. to −196° C. in the freezing treatment, and wherein the frozen fluid is subjected to a thawing treatment to a temperature of up to 50° C.

3. The method of claim 1, wherein the freezing treatment is carried out with a cooling rate of about 1260° C./min to about 12600° C./min.

4. The method of claim 1, wherein the whole blood comprises a Hematocrit level between 0.1 and 0.6.

5. The method of claim 1 which does not include
(i) a sedimentation and/or precipitation step and/or centrifugation step and/or
(ii) an addition of chemical lysis reagents before the freezing/thawing procedure.

6. A method of determining an analyte in a whole blood sample comprising cellular components, comprising:
processing the whole blood sample comprising cellular components according to the method of claim 1, and
determining presence of the analyte in the processed whole blood sample.

7. The method of claim 6 wherein the analyte is a biological compound selected from the group consisting of nucleic acids, polypeptides, peptides, lipids, sugars, hormones, metabolites and pharmaceutical compounds.

8. The method of claim 7, wherein the pharmaceutical compound is an immunosuppressive drug selected from the group consisting of cyclosporin, rapamycin and tacrolimus.

9. A method of determining an immunosuppressive drug in a whole blood sample, comprising:
processing the whole blood sample comprising an immunosuppressive drug according to the method of claim 1, and
determining the presence of the immunosuppressive drug in the processed whole blood sample.

10. A method of determining a clinical-chemical parameter in a whole blood sample from a newborn, comprising
processing the whole blood sample comprising a clinical-chemical parameter according to the method of claim 1, and
determining the presence of the clinical-chemical parameter in the processed whole blood sample from a newborn.

11. The method of claim 1, wherein the fluid is frozen to a temperature of −120° C. to −190° C. in the freezing treatment, and wherein the frozen fluid is subjected to a thawing treatment to a temperature of up to 40° C.

12. The method of claim 1, wherein the fluid is frozen to a temperature of −120° C. to −190° C. in the freezing treatment, and wherein the frozen fluid is subjected to a thawing treatment to a temperature of up to room temperature.

13. The method of claim 1, wherein the freezing treatment is carried out with a cooling rate of about 2000-4000° C./min.

* * * * *